United States Patent
Jin et al.

(10) Patent No.: US 8,119,989 B2
(45) Date of Patent: Feb. 21, 2012

(54) DEVICE AND METHOD FOR TERAHERTZ IMAGING WITH COMBINING TERAHERTZ TECHNOLOGY AND AMPLITUDE-DIVISION INTERFERENCE TECHNOLOGY

(75) Inventors: Lei Jin, Shenzhen (CN); Yuanting Zhang, Shenzhen (CN); Xiaojing Gong, Shenzhen (CN); Jun Yang, Shenzhen (CN); Yandong Zhang, Shenzhen (CN)

(73) Assignee: Shenzhen Institute of Advanced Technology, Shenzhen (CN)

( * ) Notice: Subject to any disclaimer, the term of this patent is extended or adjusted under 35 U.S.C. 154(b) by 0 days.

(21) Appl. No.: 12/457,790

(22) Filed: Jun. 22, 2009

(65) Prior Publication Data
US 2010/0282968 A1    Nov. 11, 2010

(30) Foreign Application Priority Data
May 7, 2009    (CN) .......................... 2009 1 0135979

(51) Int. Cl.
*G01J 5/02*    (2006.01)

(52) U.S. Cl. .................................................. 250/341.1
(58) Field of Classification Search ................ 250/341.1
See application file for complete search history.

(56) References Cited

U.S. PATENT DOCUMENTS

| | | | |
|---|---|---|---|
| 2002/0085209 A1* | 7/2002 | Mittleman et al. ............ 356/497 |
| 2002/0153874 A1* | 10/2002 | Jiang et al. ....................... 324/96 |
| 2006/0113480 A1* | 6/2006 | Tribe ........................ 250/370.08 |
| 2007/0195921 A1* | 8/2007 | Ouchi ................................ 378/1 |
| 2007/0263682 A1* | 11/2007 | Zhang et al. ..................... 372/25 |
| 2008/0074674 A1* | 3/2008 | Chen et al. ..................... 356/502 |
| 2008/0165355 A1* | 7/2008 | Yasui et al. .................... 356/323 |
| 2008/0203306 A1* | 8/2008 | Zhang et al. ............... 250/341.1 |

* cited by examiner

*Primary Examiner* — David Porta
*Assistant Examiner* — Marcus Taningco
(74) *Attorney, Agent, or Firm* — Rosenberg, Klein & Lee

(57) ABSTRACT

This invention provides a device and a method for THz imaging to obtain real 3D image of sample and achieve high resolution, by combining THz technology and amplitude-division interference technology.

20 Claims, 2 Drawing Sheets

DEVICE AND METHOD FOR TERAHERTZ IMAGING WITH COMBINING TERAHERTZ TECHNOLOGY AND AMPLITUDE-DIVISION INTERFERENCE TECHNOLOGY

FIELD OF THE INVENTION

The present invention relates to an imaging technology, in particular, relates to a device and a method for Terahertz (THz) imaging combining THz technology and amplitude-division interference technology.

BACKGROUND OF THE INVENTION

THz radiation can penetrate most of non-polarity dielectric, so the THz radiation can be acted as information carrier in imaging technology. In THz imaging technology, time waveform of THz pulse of each measure point of sample is recorded, then spectrum information of the measure point is obtained from Fourier transform of the time waveform. Therefore, not only contour but also components of the sample can be obtained from THz imaging technology. Moreover, refractive index distribution (depth distribution) can be calculated from time interval (phase change) of THz pulse.

Transmission mode or reflection mode is used in the THz imaging technology of prior art, and 2D image of sample can be obtained. Furthermore, 3D structure information of the sample can be obtained from time interval of the reflected THz pulse or by computer-aided tomography. But the THz imaging technology of prior art has not intrinsic 3D imaging ability.

Although real 3D image of sample by utilizing THz technology is desired, this technical difficulty is not solved so far.

This invention intends to provide a device and a method for THz imaging to solve the problem above.

SUMMARY OF THE INVENTION

The object of the present invention is to provide a device and a method for THz imaging to obtain real 3D image of samples and achieve high resolution, by combining THz technology and amplitude-division interference technology.

To accomplish this object, the present invention is characterized by a device for THz imaging. The device comprises: a THz pulse emitter emitting THz pulses; an amplitude-division interferometer receiving the THz pulses, splitting each THz pulse into a reference beam and a signal beam, and making an optical path difference between the reference path and the signal path being less than a length of wave train, and a detector. The signal beam is used for scanning sample; the reference beam and the signal beam interfere with each other, then THz pulse amplitude-division interference signals containing sample information are generated; the detector receives the THz pulse amplitude-division interference signals and generates electrical signals containing the sample information.

The invention is also characterized by a method for THz imaging. The method comprises: emitting THz pulses; splitting each THz pulse into a reference beam and a signal beam, and making an optical path difference between the reference path and the signal path being less than a length of wave train; generating THz pulse amplitude-division interference signals containing sample information; receiving the THz pulse amplitude-division interference signals; and generating electrical signals containing the sample information.

The THz imaging device has intrinsic 3D imaging ability and high resolution, by combining THz technology and amplitude-division interference technology. So the invention solves the technical difficulty and has unexpected technical effect. The invention can be regard as a pioneer invention, compared with the THz imaging technology of prior art.

Furthermore, the THz imaging device has high SNR, by modulating phase of the reference beam.

BRIEF DESCRIPTION OF THE DRAWINGS

Example embodiments of the invention with refinements will be explained hereafter. Examples set forth do not constitute a restriction of the invention. In particular, the size ratios are purely schematic. In the drawings.

DESCRIPTION OF THE PREFERRED EMBODIMENT

Figure 1:
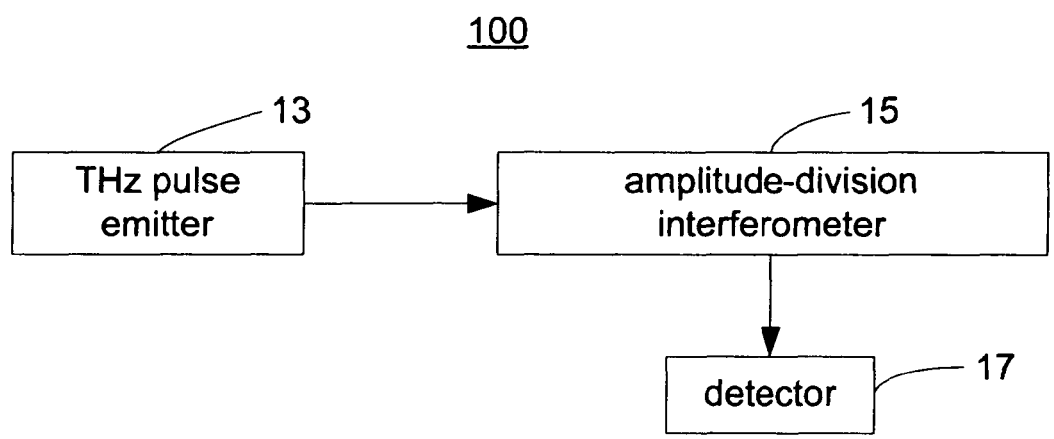
FIG. 1 shows a schematic illustration of a THz imaging device.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Figure 2:
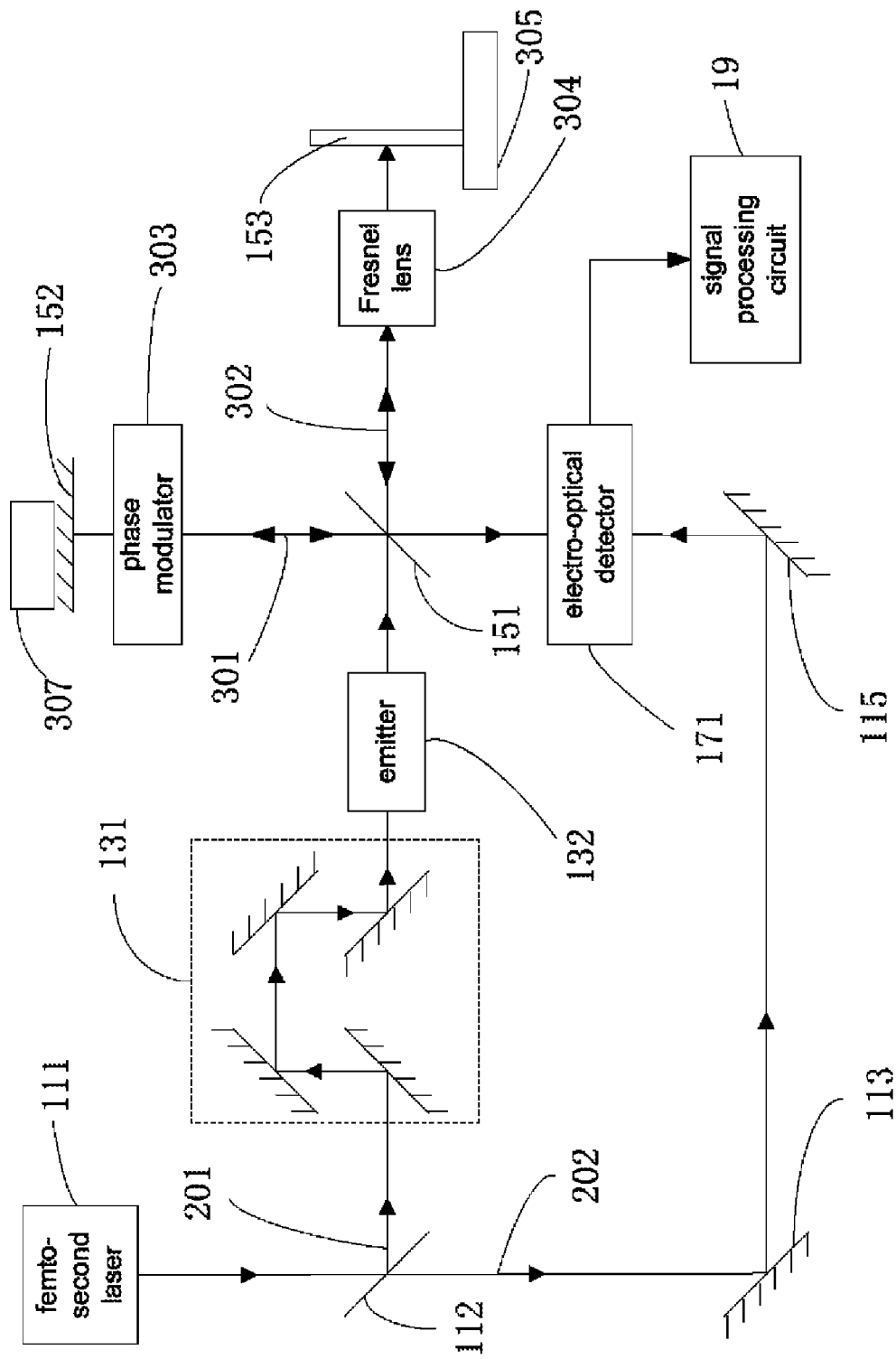
FIG. 2 shows a preferred embodiment of the THz imaging device of FIG. 1.

FIG. 1 shows a schematic illustration of a THz imaging device, and FIG. 2 shows a preferred embodiment of the THz imaging device of FIG. 1. The THz imaging device 100 includes a THz pulse emitter 13, an amplitude-division interferometer 15, and a detector 17.

The THz pulse emitter 13 is an optical rectification emitter, and includes a laser part, a time-delay device 131, and an emitter 132. The laser includes a femto-second laser 111, a first beam splitter 112, a first reflector 113, and a second reflector 115. The amplitude-division interferometer 15 includes a second beam splitter 151, a reference minor 152, and a sample platform 305. The sample platform 305 is used for carrying the sample 153. The detector 17 is an electro-optical detector 171 (electrooptical crystal), such as zinc telluride, gallium arsenide, and so on.

The first beam splitter 112 splits each femto-second beam emitted from the femto-second laser 111 into a pump beam and a probe beam. The pump beam 201 transmits through the time-delay device 131 and reaches the emitter 132. The emitter 132 is used for emitting THz pulses. The probe beam 202 is reflected by the first reflector 113 and the second reflector 115, then reaches the electro-optical detector 171. The time-delay device 131 is used for changing relative delay time between the pump beam 201 and the probe beam 202.

In alternative embodiment, the time-delay device 131 is placed between the first beam splitter 112 and the electro-optical detector 171. In this case, the time-delay device 131 is used for changing relative delay time between the probe beam 202 and the pump beam 201.

The reference mirror 152 can be a plane mirror. The reference minor 152 is moved along propagation direction of the reference beam 301 under the control of an electro-motor 307. Doppler shift can be obtained by moving the reference mirror 152. The THz pulse emitted from the emitter 132 reaches the second beam splitter 151, and the second beam splitter 151 splits the THz pulse into a reference beam 301 and a signal beam 302. The reference beam 301 is reflected by the reference minor 152, then transmits through the second beam splitter 151 and propagates towards the electro-optical detector 171. The signal beam 302 is reflected by the sample 153, then reaches the second beam splitter 151 and is reflected by the second beam splitter 151. The signal beam 302 also propagates towards the electro-optical detector 171. When an optical path difference between the reference beam 301 and the signal beam 302 is less than a length of wave train, the reference beam 301 and the signal beam 302 interfere with each other, and THz pulse amplitude-division interference signals (interference patterns) are generated correspondingly. The electro-optical detector 171 receives the THz pulse amplitude-division interference signals. The THz pulse amplitude-division interference signals contain sample information, such as 3D structure information of the sample, spectrum information of the sample, and so on.

In alternative embodiment, the amplitude-division interferometer 15 further includes phase modulator 303, the phase modulator 303 is placed between the second beam splitter 151 and the reference mirror 152. The phase modulator 303 is used for modulating phase of the reference beam 301. The sample information loaded on specific frequencies keeps from being submerged in noise by modulating the reference beam 301. In this embodiment, the THz imaging device 100 has high SNR.

Electrical field intensity of the reference beam 301 can be expressed as follows:

$$E_R = A_R e^{i[\omega t + \phi_R(t)]} \quad (1)$$

Where $A_R$ is amplitude of the reference beam 301, $\omega$ is circular frequency of the reference beam 301, and $\phi_R(t)$ is modulated phase.

Electrical field intensity of the signal beam 302 can be expressed as follows:

$$E_S = A_S e^{i[(\omega + \Delta\omega)t + \phi_S]} \quad (2)$$

Where $A_S$ is amplitude of the signal beam 302, $\omega$ is circular frequency of the signal beam 302, $\Delta\omega$ is frequency excursion of the signal beam 302 after being reflected by the sample 153, $\phi_S$ is phase of the signal beam 302.

Electrical field intensity of the THz pulse amplitude-division interference signal can be expressed as follows:

$$E = E_R + E_S \quad (3)$$

$$E^* = E_R^* + E_S^* \quad (4)$$

Where $E^*$, $E_R^*$, and $E_S^*$ are conjugate electrical field intensity of E, $E_R$, and $E_S$, respectively.

According to theory of physics, luminous intensity is merely determined by electrical field component of electromagnetic wave. Therefore, luminous intensity of the THz pulse amplitude-splitting interference signal can be expressed as follows:

$$I = (E_R + E_S)(E_R^* + E_S^*) \quad (5)$$

$$I = \frac{1}{2}|A_R|^2 + \frac{1}{2}|A_S|^2 + 2A_R A_S \cos[\Delta\omega t + \phi_S - \phi_R(t)] \quad (6)$$

Where $$\frac{1}{2}|A_R|^2$$

is direct-current component of the modulated reference beam 301, $$\frac{1}{2}|A_S|^2$$

is direct-current component of the modulated signal beam 302, and $2A_R A_S \cos[\Delta\omega t + \phi_S - \phi_R(t)]$ is real part of the interference signal. The real part of the interference signal is merely determined by $\Delta\omega$, $\phi_S$, and $\phi_R(t)$. The real part of the interference signal contains the sample information.

The electro-optical detector 171 is used for detecting the THz pulse amplitude-division interference signals according to birefrigent effect of electro-optical crystal. When the THz pulse amplitude-division interference signal transmits through the electro-optical detector 171, instantaneous birefrigent effect of the electro-optical detector 171 occurs. Polarization of the probe beam 202 changes from linear polarization to elliptic polarization when the probe beam 202 transmits through the electro-optical detector 171. Electrical field intensity of the THz pulse amplitude-division interference signal is obtained by measuring degree of elliptic polarization of the probe beam 202. Therefore, the electro-optical detector 171 is used for transforming optical signals into electrical signals.

In alternative embodiment, the THz imaging device 100 further includes a Fresnel lens 304. The Fresnel lens 304 is placed between the second beam splitter 151 and the sample 153. NA of the Fresnel lens 304 is greater than or equal to 0.7. In this embodiment, the THz imaging device 100 has sub-millimeter lateral resolution.

The THz imaging device 100 further includes a signal processing circuit 19. The signal processing circuit 19 is used for processing (amplifying, filtering, demodulating, and so on) the electrical signals output from the electro-optical detector 171 and outputting amplitude and phase information of the THz pulse amplitude-division interference signals.

A method of demodulating signals is as follows.

Let a signal is f(t), its Hilbert's transform is:

$$\tilde{f}(t) = H[f(t)] = \frac{1}{\pi}\int_{-\infty}^{+\infty} \frac{f(\tau)}{t-\tau} d\tau = f(t) * \frac{1}{\pi t} \quad (7)$$

Where H is Hilbert's transform, f(t) and $\tilde{f}(t)$ are orthogonal.

Let a complex signal is $z(t) = f(t) + j\tilde{f}(t)$, and let $f(t) = a(t)\cos\theta(t)$, an orthogonal component of f(t) is $\tilde{f}(t) = a(t)\sin\theta(t)$, the complex signal is $z(t) = a(t)\cos\theta(t) + ja(t)\sin\theta(t) = a(t)e^{j\theta(t)}$. Amplitude and phase of f(t) can be calculated:

$$a(t) = \sqrt{f^2(t) + \tilde{f}^2(t)} \quad (8)$$

$$\theta(t) = \arctan\left\{\frac{\text{Im}[z(t)]}{\text{Re}[z(t)]}\right\} = \arctan\left\{\frac{f(t)}{\tilde{f}(t)}\right\} \quad (9)$$

Visual images can be obtained by digital processing the output of the signal processing circuit. The digital processing includes resampling, quantification, pseudo-color staining, and so on. The digital processing can be implemented by a computer.

In the THz imaging device 100, axial scan is achieved by moving the reference mirror 152, and axial structure information of the sample 153 is obtained by axial scan. Lateral scan consists of a series of axial scans. 3D structure information of the sample 153 is obtained by combining the axial scans and the lateral scans.

In alternative embodiment, the amplitude-division interferometer 15 can be replaced by a Michelson's interferometer or other optical instrument realizing amplitude-division interference.

In alternative embodiment, the THz pulse emitter 13 can be a photoconductive emitter.

In alternative embodiment, the detector 17 can be a photoconductive detector.

Atomic radiation is not a simple harmonic wave, but a series of wave trains. Phase difference between any two wave trains is not constant. Therefore, interference occurs merely when two sub-wave-trains belonging to the same wave train meet at a superposition point. Because the wave train of the THz pulse is short, interference occurs merely when the optical path difference between the reference beam 301 and the signal beam 302 is smaller than a length of wave train. Thus, the THz imaging device 100 has high spatial location.

The amplitude-division interferometer 15 can be regarded as a Michelson's interferometer, therefore, the THz imaging device 100 has micron axial resolution and sub-millimeter lateral resolution. The THz imaging device 100 ingeniously utilizes amplitude-division interference principle of the Michelson's interferometer and special signal modulating technology. Therefore, detecting sample with non-destructive, non-contact, and long working distance can be achieved. Imaging with real time, non-destructive, and original position can also be achieved.

The THz imaging device 100 can be applied in many fields, such as medical testing, safety inspection, jade identification, mining, archeology identification, and so on.

Although only limited example embodiments are described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A device for THz imaging comprising:
   a THz pulse emitter emitting THz pulses;
   an amplitude-division interferometer receiving the THz pulses, splitting each THz pulse into a reference beam and a signal beam, and making an optical path length difference between the reference beam and the signal beam being less than a length of a wave train via axial displacement of a mirror to maintain an optical path difference, and
   a detector;
   wherein the signal beam is used for scanning a sample; the reference beam and the signal beam interfere with each other, then THz pulse amplitude-division interference signals containing sample information are generated; the detector receives the THz pulse amplitude-division interference signals and generates electrical signals containing the sample information.

2. The device as claimed in claim 1, wherein the amplitude-division interferometer is a Michelson's interferometer.

3. The device as claimed in claim 1, wherein the THz pulse emitter is an optical rectification emitter or a photoconductive emitter, the detector is an electro-optical detector or a photoconductive detector.

4. The device as claimed in claim 3, wherein the electro-optical detector is an electro-optical crystal.

5. The device as claimed in claim 4, wherein the electro-optical crystal is zinc telluride or gallium arsenide.

6. The device as claimed in claim 3, wherein the optical rectification emitter comprises a laser part, a time-delay device, and an emitter; the laser outputs pump beam and probe beam; the pump beam transmits through the time-delay device and reaches the emitter; the probe beam reaches the detector; the time-delay device is used for changing relative delay time between the pump beam and the probe beam; the emitter is used for emitting THz pulse.

7. The device as claimed in claim 3, wherein the optical rectification emitter comprises a laser part, a time-delay device, and an emitter; the laser outputs pump beam and probe beam; the pump beam reaches the emitter; the probe beam transmits through the time-delay device and reaches the detector; the time-delay device is used for changing relative delay time between the probe beam and the pump beam; the emitter is used for emitting THz pulse.

8. The device as claimed in claim 7, wherein the laser part comprises a femto-second laser and a beam splitter; the beam splitter splits the femto-second beam emitted from the femto-second laser into the pump beam and the probe beam.

9. The device as claimed in claim 1, wherein the amplitude-division interferometer comprises a beam splitter, a reference mirror, and a sample platform; the sample platform is used for carrying the sample; the beam splitter splits the THz pulse into the reference beam and the signal beam; the reference beam is reflected by the reference mirror, then transmits through the beam splitter and propagates towards the detector; the signal beam is reflected by the sample, then reaches the beam splitter and is reflected by the beam splitter, then the signal beam propagates towards the detector.

10. The device as claimed in claim 9, wherein the reference mirror can be moved along propagation direction of the reference beam.

11. The device as claimed in claim 10, wherein the reference mirror is a plane mirror and is controlled by an electromotor.

12. The device as claimed in claim 9, wherein the amplitude-division interferometer further includes a phase modulator, the phase modulator is placed between the beam splitter and the reference mirror.

13. The device as claimed in claim 9, wherein the amplitude-division interferometer further includes a Fresnel lens, the Fresnel lens is placed between the beam splitter and the sample.

14. The device as claimed in claim 1, wherein NA of the Fresnel lens is greater than or equal to 0.7.

15. The device as claimed in claim 1, wherein the sample information comprises 3D structure information and spectrum information of the sample.

16. The device as claimed in claim 1, further comprising a signal processing circuit, the signal processing circuit is used for processing the electrical signals and outputting amplitude and phase information of the THz pulse amplitude-division interference signals.

17. The device as claimed in claim 16, further comprising a computer, wherein the computer is used for digital processing the output of the signal processing circuit and outputting visual images.

18. A method for THz imaging comprising:
    emitting THz pulses;
    splitting each THz pulse into a reference beam and a signal beam, and axially displacing a mirror to make an optical path length difference between the reference beam and the signal beam less than a length of a wave train;
    generating THz pulse amplitude-division interference signals containing sample information;
    receiving the THz pulse amplitude-division interference signals; and
    generating electrical signals containing the sample information.

19. The method as claimed in claim 18, further comprising: processing the electrical signals; and
    outputting visual images containing 3D structure information and spectrum information of the sample.

20. The method as claimed in claim 18, further comprising: modulating phase of the reference beam.

\* \* \* \* \*